US007831305B2

(12) United States Patent
Gliner (10) Patent No.: US 7,831,305 B2
(45) Date of Patent: Nov. 9, 2010

(54) NEURAL STIMULATION SYSTEM AND METHOD RESPONSIVE TO COLLATERAL NEURAL ACTIVITY

(75) Inventor: Bradford Evan Gliner, Sammamish, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 519 days.

(21) Appl. No.: 10/271,394

(22) Filed: Oct. 15, 2002

(65) Prior Publication Data
US 2003/0074032 A1   Apr. 17, 2003

Related U.S. Application Data

(63) Continuation-in-part of application No. 09/978,134, filed on Oct. 15, 2001, now Pat. No. 7,305,268.

(51) Int. Cl.
*A61N 1/08* (2006.01)
(52) U.S. Cl. .................................. 607/45; 607/46
(58) Field of Classification Search ............. 607/44–46, 607/1, 2, 62
See application file for complete search history.

(56) References Cited

U.S. PATENT DOCUMENTS

| | | | |
|---|---|---|---|
| 2,716,226 A | 8/1955 | Jonas | |
| 2,721,316 A | 10/1955 | Shaw | |
| 3,595,962 A * | 7/1971 | Aldrich | 514/424 |
| 3,628,193 A | 12/1971 | Collins | |
| 3,650,276 A | 3/1972 | Burghele et al. | |
| 3,654,933 A | 4/1972 | Hagfors | |
| 3,850,161 A | 11/1974 | Liss | |
| 3,918,461 A | 11/1975 | Cooper | |
| 4,019,518 A | 4/1977 | Maurer et al. | |
| 4,030,509 A | 6/1977 | Heilman et al. | |
| 4,125,116 A | 11/1978 | Fischell | |

(Continued)

FOREIGN PATENT DOCUMENTS

DE       19750043 A1    5/1999

(Continued)

OTHER PUBLICATIONS

U.S. Appl. No. 09/802,808, filed Mar. 8, 2001, Firlik.

(Continued)

*Primary Examiner*—Michael Kahelin
(74) *Attorney, Agent, or Firm*—Melissa Acosta; Christopher S. L. Crawford; Peter Lando (57) ABSTRACT

A neural stimulation system responsive to collateral neural activity that may arise in association with a neural stimulation procedure includes a stimulation interface configured to deliver stimulation signals to a target neural population, a monitoring interface positioned to receive signals corresponding to a neural activity within the target neural population, a stimulus unit coupled to deliver stimulation signals to the stimulation interface, and a sensing unit coupled to the monitoring device and the stimulus unit. The neural stimulation procedure may be directed toward rehabilitating, restoring, and/or enhancing one or more neural functions by facilitating and/or effectuating a neuroplastic change or reorganization; and/or affecting a neurological condition that exists on a continuous or essentially continuous basis absent the stimulation procedure. The sensing unit determines whether evidence of an collateral neural activity exists, whereupon the stimulus unit attempts to abate the collateral neural activity.

17 Claims, 6 Drawing Sheets

U.S. PATENT DOCUMENTS

| | | | |
|---|---|---|---|
| 4,140,133 A | | 2/1979 | Kastrubin et al. |
| 4,214,804 A | | 7/1980 | Little |
| 4,245,645 A | | 1/1981 | Arseneault et al. |
| 4,308,868 A | | 1/1982 | Jhabvala |
| 4,328,813 A | | 5/1982 | Ray |
| 4,340,038 A | | 7/1982 | McKean |
| 4,341,221 A | | 7/1982 | Testerman |
| 4,390,023 A | | 6/1983 | Rise |
| 4,431,000 A | | 2/1984 | Butler et al. |
| 4,474,186 A | | 10/1984 | Ledley et al. |
| 4,541,432 A | | 9/1985 | Molina-Negro et al. |
| 4,542,752 A | | 9/1985 | DeHaan et al. |
| 4,590,946 A | | 5/1986 | Loeb |
| 4,607,639 A | | 8/1986 | Tanagho et al. |
| 4,646,744 A | | 3/1987 | Capel |
| 4,702,254 A | | 10/1987 | Zabara |
| 4,774,967 A | | 10/1988 | Zanakis |
| 4,779,630 A | | 10/1988 | Scharnberg |
| 4,817,634 A | | 4/1989 | Holleman et al. |
| 4,844,075 A | * | 7/1989 | Liss et al. ............... 607/45 |
| 4,865,048 A | | 9/1989 | Eckerson |
| 4,869,225 A | | 9/1989 | Nagata et al. |
| 4,903,702 A | | 2/1990 | Putz |
| 4,949,140 A | | 8/1990 | Tam |
| 4,969,468 A | | 11/1990 | Byers et al. |
| 4,983,322 A | | 1/1991 | Elsenbaumer |
| 5,002,053 A | | 3/1991 | Garcia-Rill et al. |
| 5,024,226 A | | 6/1991 | Tan |
| 5,030,225 A | | 7/1991 | Aebischer |
| 5,031,618 A | | 7/1991 | Mullett |
| 5,044,368 A | | 9/1991 | Putz |
| 5,054,906 A | | 10/1991 | Lyons, Jr. et al. |
| 5,063,932 A | | 11/1991 | Dahl et al. |
| 5,073,114 A | | 12/1991 | Detsch |
| 5,092,835 A | | 3/1992 | Schurig et al. |
| 5,121,754 A | | 6/1992 | Mullett |
| 5,130,412 A | | 7/1992 | Wellinghoff |
| 5,143,089 A | | 9/1992 | Alt |
| 5,169,384 A | | 12/1992 | Bosniak et al. |
| 5,184,620 A | | 2/1993 | Cudahy et al. |
| 5,193,540 A | | 3/1993 | Schulman et al. |
| 5,215,086 A | | 6/1993 | Terry, Jr. et al. |
| 5,215,088 A | | 6/1993 | Normann et al. |
| 5,224,491 A | | 7/1993 | Mehra |
| 5,255,678 A | | 10/1993 | Deslauriers |
| 5,263,967 A | | 11/1993 | Lyons, III et al. |
| 5,269,302 A | * | 12/1993 | Swartz et al. ............... 607/45 |
| 5,269,303 A | | 12/1993 | Wernicke et al. |
| 5,271,417 A | | 12/1993 | Swanson et al. |
| 5,282,468 A | | 2/1994 | Klepinski |
| 5,299,569 A | | 4/1994 | Wernicke et al. |
| 5,303,705 A | | 4/1994 | Nenov |
| 5,304,206 A | | 4/1994 | Baker, Jr. et al. |
| 5,314,458 A | | 5/1994 | Najafi |
| 5,330,520 A | | 7/1994 | Maddison |
| 5,358,513 A | | 10/1994 | Powell, III et al. |
| 5,358,514 A | | 10/1994 | Schulman et al. |
| 5,370,672 A | | 12/1994 | Fowler et al. |
| 5,405,375 A | | 4/1995 | Ayers et al. |
| 5,406,957 A | | 4/1995 | Tansey |
| 5,411,540 A | | 5/1995 | Edell et al. |
| 5,417,719 A | | 5/1995 | Hull et al. |
| 5,423,864 A | | 6/1995 | Ljungstroem |
| 5,441,528 A | | 8/1995 | Chang et al. |
| 5,464,446 A | | 11/1995 | Dreessen et al. |
| 5,470,846 A | | 11/1995 | Sandyk |
| 5,520,190 A | | 5/1996 | Benedict et al. |
| 5,522,864 A | | 6/1996 | Wallace et al. |
| 5,537,512 A | | 7/1996 | Hsia et al. |
| 5,540,734 A | | 7/1996 | Zabara |
| 5,540,736 A | | 7/1996 | Haimovich et al. |
| 5,549,655 A | | 8/1996 | Erickson |
| 5,562,708 A | | 10/1996 | Combs et al. |
| 5,575,813 A | | 11/1996 | Edell et al. |
| 5,591,216 A | | 1/1997 | Testerman et al. |
| 5,593,432 A | | 1/1997 | Crowther et al. |
| 5,601,611 A | | 2/1997 | Fayram et al. |
| 5,611,350 A | | 3/1997 | John |
| 5,618,531 A | | 4/1997 | Cherksey |
| 5,628,317 A | | 5/1997 | Starkebaum et al. |
| 5,641,680 A | | 6/1997 | Zhao |
| 5,674,251 A | | 10/1997 | Combs et al. |
| 5,674,264 A | | 10/1997 | Carter et al. |
| 5,676,655 A | | 10/1997 | Howard, III et al. |
| 5,683,422 A | | 11/1997 | Rise |
| 5,690,927 A | | 11/1997 | Major |
| 5,702,429 A | | 12/1997 | King |
| 5,707,334 A | | 1/1998 | Young |
| 5,711,316 A | | 1/1998 | Elsberry et al. |
| 5,713,922 A | | 2/1998 | King |
| 5,713,923 A | | 2/1998 | Ward et al. |
| 5,716,377 A | | 2/1998 | Rise et al. |
| 5,722,401 A | | 3/1998 | Pietroski |
| 5,735,814 A | | 4/1998 | Elsberry et al. |
| 5,750,376 A | | 5/1998 | Weiss et al. |
| 5,752,979 A | | 5/1998 | Benabid |
| 5,753,502 A | | 5/1998 | Kilgannon |
| 5,753,505 A | | 5/1998 | Luskin |
| 5,767,252 A | | 6/1998 | Worley |
| 5,769,778 A | | 6/1998 | Abrams et al. |
| 5,772,591 A | | 6/1998 | Cram |
| 5,782,798 A | | 7/1998 | Rise |
| 5,782,873 A | | 7/1998 | Collins |
| 5,792,186 A | | 8/1998 | Rise |
| 5,792,188 A | | 8/1998 | Starkweather et al. |
| 5,797,970 A | | 8/1998 | Pouvreau |
| 5,814,014 A | | 9/1998 | Elsberry et al. |
| 5,814,092 A | | 9/1998 | King |
| 5,817,075 A | | 10/1998 | Giungo |
| 5,817,784 A | | 10/1998 | Theill |
| 5,824,021 A | | 10/1998 | Rise |
| 5,824,030 A | | 10/1998 | Yang et al. |
| 5,832,932 A | | 11/1998 | Elsberry et al. |
| 5,833,603 A | | 11/1998 | Kovacs et al. |
| 5,833,709 A | | 11/1998 | Rise et al. |
| 5,840,689 A | | 11/1998 | Daniloff |
| 5,843,148 A | | 12/1998 | Gijsbers et al. |
| 5,843,150 A | | 12/1998 | Dreessen et al. |
| 5,846,196 A | | 12/1998 | Siekmeyer et al. |
| 5,859,197 A | | 1/1999 | Theill |
| 5,865,842 A | | 2/1999 | Knuth et al. |
| 5,871,517 A | | 2/1999 | Abrams et al. |
| 5,885,976 A | | 3/1999 | Sandyk |
| 5,886,769 A | | 3/1999 | Zolten |
| 5,893,883 A | | 4/1999 | Torgerson et al. |
| 5,904,916 A | | 5/1999 | Hirsch |
| 5,913,882 A | | 6/1999 | King |
| 5,916,171 A | | 6/1999 | Mayevsky |
| 5,925,070 A | | 7/1999 | King et al. |
| 5,928,144 A | | 7/1999 | Real |
| 5,938,688 A | | 8/1999 | Schiff |
| 5,938,689 A | | 8/1999 | Fischell |
| 5,941,906 A | | 8/1999 | Barreras, Sr. et al. |
| 5,962,027 A | | 10/1999 | Hughes |
| 5,964,794 A | | 10/1999 | Bolz et al. |
| 5,975,085 A | | 11/1999 | Rise |
| 5,978,702 A | | 11/1999 | Ward et al. |
| 5,983,140 A | | 11/1999 | Smith et al. |
| 5,999,584 A | | 12/1999 | Adams et al. |
| 6,006,124 A | | 12/1999 | Fischell |
| 6,011,996 A | | 1/2000 | Gielen et al. |
| 6,016,449 A | | 1/2000 | Fischell |
| 6,018,682 A | | 1/2000 | Rise |
| 6,021,352 A | | 2/2000 | Christopherson et al. |

| Patent | Date | Inventor |
|---|---|---|
| 6,024,702 A | 2/2000 | Iversen |
| 6,026,326 A | 2/2000 | Bardy |
| 6,035,236 A | 3/2000 | Jarding et al. |
| 6,036,678 A | 3/2000 | Giungo |
| 6,038,480 A | 3/2000 | Hrdlicka et al. |
| 6,040,180 A | 3/2000 | Johe |
| 6,042,579 A | 3/2000 | Elsberry et al. |
| 6,051,017 A | 4/2000 | Loeb et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,078,838 A | 6/2000 | Rubinstein |
| 6,082,364 A | 7/2000 | Balian |
| 6,094,598 A | 7/2000 | Elsberry et al. |
| 6,095,148 A | 8/2000 | Shastri |
| 6,104,956 A | 8/2000 | Naritoku et al. |
| 6,104,960 A | 8/2000 | Duysens et al. |
| 6,111,911 A | 8/2000 | Sanderford, Jr. et al. |
| 6,122,548 A | 9/2000 | Starkebaum et al. |
| 6,126,657 A | 10/2000 | Edwards et al. |
| 6,128,527 A | 10/2000 | Howard, III et al. |
| 6,128,537 A * | 10/2000 | Rise .......................... 607/45 |
| 6,128,538 A | 10/2000 | Fischell |
| 6,132,361 A | 10/2000 | Epstein et al. |
| 6,134,474 A | 10/2000 | Fischell |
| 6,149,612 A | 11/2000 | Schnapp et al. |
| 6,151,525 A | 11/2000 | Soykan |
| 6,152,143 A | 11/2000 | Edwards |
| 6,152,882 A | 11/2000 | Prutchi |
| 6,161,044 A | 12/2000 | Silverstone |
| 6,161,045 A | 12/2000 | Fischell |
| 6,161,047 A | 12/2000 | King et al. |
| 6,176,242 B1 | 1/2001 | Rise |
| 6,190,893 B1 | 2/2001 | Shastri |
| 6,198,958 B1 | 3/2001 | Ives et al. |
| 6,205,360 B1 | 3/2001 | Carter et al. |
| 6,205,361 B1 | 3/2001 | Kuzma et al. |
| 6,208,893 B1 | 3/2001 | Hofmann |
| 6,210,417 B1 | 4/2001 | Baudino et al. |
| 6,214,334 B1 | 4/2001 | Lee |
| 6,221,908 B1 | 4/2001 | Kilgard |
| 6,227,203 B1 | 5/2001 | Rise et al. |
| 6,230,049 B1 * | 5/2001 | Fischell et al. .............. 600/544 |
| 6,233,480 B1 | 5/2001 | Hochman |
| 6,236,892 B1 | 5/2001 | Feler |
| 6,238,429 B1 | 5/2001 | Markowitz |
| 6,245,566 B1 | 6/2001 | Gearhart |
| 6,246,912 B1 | 6/2001 | Sluijter |
| 6,263,225 B1 | 7/2001 | Howard |
| 6,263,237 B1 | 7/2001 | Rise |
| 6,264,944 B1 | 7/2001 | Smith |
| 6,280,462 B1 | 8/2001 | Hauser et al. |
| 6,301,493 B1 | 10/2001 | Marro et al. |
| 6,304,787 B1 | 10/2001 | Kuzma et al. |
| 6,319,241 B1 | 11/2001 | King et al. |
| 6,339,725 B1 | 1/2002 | Naritoku et al. |
| 6,353,754 B1 | 3/2002 | Fischell |
| 6,353,762 B1 | 3/2002 | Baudino et al. |
| 6,354,299 B1 | 3/2002 | Fischell |
| 6,356,786 B1 | 3/2002 | Rezai et al. |
| 6,356,792 B1 | 3/2002 | Errico et al. |
| 6,360,122 B1 | 3/2002 | Fischell |
| 6,366,813 B1 * | 4/2002 | DiLorenzo .................. 607/45 |
| 6,375,666 B1 | 4/2002 | Mische |
| 6,381,496 B1 | 4/2002 | Meadows et al. |
| 6,393,319 B1 | 5/2002 | Bock et al. |
| 6,405,079 B1 | 6/2002 | Ansarinia |
| 6,418,344 B1 | 7/2002 | Rezai |
| 6,421,566 B1 * | 7/2002 | Holsheimer .................. 607/46 |
| 6,425,852 B1 | 7/2002 | Epstein et al. |
| 6,427,086 B1 | 7/2002 | Fischell |
| 6,456,886 B1 | 9/2002 | Howard, III et al. |
| 6,459,936 B2 | 10/2002 | Fischell |
| 6,463,328 B1 | 10/2002 | John |
| 6,464,356 B1 | 10/2002 | Sabel et al. |
| 6,466,822 B1 * | 10/2002 | Pless .......................... 607/45 |
| 6,473,568 B2 | 10/2002 | Kashiyama |
| 6,473,639 B1 | 10/2002 | Fischell |
| 6,480,743 B1 | 11/2002 | Kirkpatrick |
| 6,484,059 B2 | 11/2002 | Gielen |
| 6,487,450 B1 | 11/2002 | Chen |
| 6,497,699 B1 | 12/2002 | Ludvig et al. |
| 6,499,488 B1 | 12/2002 | Hunter |
| 6,505,075 B1 | 1/2003 | Weiner |
| 6,507,755 B1 | 1/2003 | Gozani et al. |
| 6,529,774 B1 | 3/2003 | Greene |
| 6,539,263 B1 | 3/2003 | Schiff et al. |
| 6,549,814 B1 | 4/2003 | Strutz et al. |
| 6,556,868 B2 | 4/2003 | Naritoku et al. |
| 6,569,654 B2 | 5/2003 | Shastri et al. |
| 6,591,138 B1 | 7/2003 | Fischell et al. |
| 6,597,954 B1 | 7/2003 | Fischell et al. |
| 6,609,030 B1 | 8/2003 | Rezai et al. |
| 6,609,031 B1 | 8/2003 | Law et al. |
| 6,615,065 B1 | 9/2003 | Barrett et al. |
| 6,622,048 B1 | 9/2003 | Mann |
| 6,631,295 B2 | 10/2003 | Rubinstein et al. |
| 6,633,780 B1 | 10/2003 | Berger |
| 6,647,296 B2 | 11/2003 | Fischell et al. |
| 6,658,299 B1 | 12/2003 | Dobelle |
| 6,665,562 B2 | 12/2003 | Gluckman et al. |
| 6,684,105 B2 | 1/2004 | Cohen et al. |
| 6,687,525 B2 | 2/2004 | Llinas |
| 6,690,974 B2 | 2/2004 | Archer |
| 6,708,064 B2 | 3/2004 | Rezai |
| 6,725,094 B2 | 4/2004 | Saberski |
| 6,735,475 B1 | 5/2004 | Whitehurst et al. |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,819,956 B2 | 11/2004 | DiLorenzo |
| 6,839,594 B2 | 1/2005 | Cohen et al. |
| 6,850,802 B2 | 2/2005 | Holsheimer |
| 6,871,098 B2 | 3/2005 | Wilof-Mindus et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,898,464 B2 | 5/2005 | Edell et al. |
| 6,907,296 B1 | 6/2005 | Doan et al. |
| 6,922,590 B1 | 7/2005 | Whitehurst |
| 6,934,580 B1 | 8/2005 | Osorio et al. |
| 6,944,497 B2 | 9/2005 | Stypulkowski |
| 6,944,501 B1 | 9/2005 | Pless |
| 6,949,081 B1 | 9/2005 | Chance |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,015,816 B2 | 3/2006 | Wildman et al. |
| 7,024,247 B2 | 4/2006 | Gliner et al. |
| 7,050,856 B2 | 5/2006 | Stypulkowski |
| 7,107,097 B2 | 9/2006 | Stern et al. |
| 7,110,820 B2 | 9/2006 | Tcheng et al. |
| 7,146,217 B2 | 12/2006 | Firlik et al. |
| 7,184,840 B2 | 2/2007 | Stolz et al. |
| 7,187,968 B2 | 3/2007 | Wolf et al. |
| 7,187,977 B2 | 3/2007 | Paul, Jr. |
| 2001/0051819 A1 | 12/2001 | Fischell et al. |
| 2002/0028072 A1 | 3/2002 | Kashiyama |

| | | |
|---|---|---|
| 2002/0058867 A1 | 5/2002 | Breiter et al. |
| 2002/0077670 A1 | 6/2002 | Archer |
| 2002/0087201 A1 | 7/2002 | Firlik et al. |
| 2002/0099295 A1 | 7/2002 | Gil et al. |
| 2002/0099412 A1 | 7/2002 | Fischell |
| 2002/0138101 A1 | 9/2002 | Suda et al. |
| 2002/0169485 A1 | 11/2002 | Pless |
| 2003/0028072 A1 | 2/2003 | Fischell et al. |
| 2003/0067963 A1 | 4/2003 | Miller et al. |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0093129 A1* | 5/2003 | Nicolelis et al. ............... 607/45 |
| 2003/0097159 A1 | 5/2003 | Schiff et al. |
| 2003/0097161 A1 | 5/2003 | Firlik et al. |
| 2003/0114886 A1 | 6/2003 | Gluckman |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0181954 A1 | 9/2003 | Rezai |
| 2003/0187490 A1 | 10/2003 | Gliner |
| 2003/0187491 A1 | 10/2003 | Greenberg et al. |
| 2003/0195602 A1 | 10/2003 | Boling |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0095990 A1 | 5/2004 | Gossett et al. |
| 2004/0102828 A1 | 5/2004 | Lowry et al. |
| 2004/0111127 A1 | 6/2004 | Gliner |
| 2004/0131998 A1 | 7/2004 | Marom et al. |
| 2004/0138550 A1 | 7/2004 | Hartlep |
| 2004/0158298 A1 | 8/2004 | Gliner et al. |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0013310 A1 | 1/2005 | Banker et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0094718 A1 | 5/2005 | Pastemak et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst et al. |
| 2005/0228451 A1 | 10/2005 | Jaax et al. |
| 2006/0004422 A1 | 1/2006 | De Ridder |
| 2006/0004423 A1 | 1/2006 | Boveja et al. |
| 2006/0015153 A1 | 1/2006 | Gliner et al. |
| 2006/0020297 A1 | 1/2006 | Gerber et al. |
| 2006/0095088 A1 | 5/2006 | De Ridder |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0166681 A1 | 7/2006 | Lohbihler |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2006/0259094 A1 | 11/2006 | Naisberg et al. |
| 2007/0032834 A1 | 2/2007 | Gliner et al. |

FOREIGN PATENT DOCUMENTS

| | | |
|---|---|---|
| EP | 0214527 | 3/1987 |
| EP | 0319844 A1 | 6/1989 |
| EP | 0 998 958 A2 | 10/2000 |
| EP | 1 145 736 | 10/2001 |
| EP | 1180056 | 11/2003 |
| WO | WO-02/09811 | 12/1987 |
| WO | WO-87/07511 | 12/1987 |
| WO | WO 87/07511 | 12/1987 |
| WO | WO-94/07564 | 4/1994 |
| WO | WO-95/21591 | 8/1995 |
| WO | WO-9726823 | 7/1997 |
| WO | WO 97-45160 | 12/1997 |
| WO | WO 98/06342 | 2/1998 |
| WO | WO-0007494 | 2/2000 |
| WO | WO-00-40295 | 7/2000 |
| WO | WO-01/12236 | 2/2001 |
| WO | WO-01/19977 | 3/2001 |
| WO | WO-01-093953 | 12/2001 |
| WO | WO 01-97906 | 12/2001 |
| WO | WO-01/97906 | 12/2001 |
| WO | WO-0197906 | 12/2001 |
| WO | WO-02/36003 | 5/2002 |
| WO | WO-02/38031 | 5/2002 |
| WO | WO-02/38217 | 5/2002 |
| WO | WO-02-073526 | 9/2002 |
| WO | WO-02072194 | 9/2002 |
| WO | WO 03/082402 | 3/2003 |
| WO | WO-03-026739 | 4/2003 |
| WO | WO 06/043690 | 5/2003 |
| WO | WO-03101532 | 12/2003 |

OTHER PUBLICATIONS

U.S. Appl. No. 60/325,872, filed Sep. 28, 2001, Sheffield.
U.S. Appl. No. 60/325,978, filed Sep. 28, 2001, Gliner.
U.S. Appl. No. 10/072,700, filed Feb. 2, 2002, Firlik.
Siebner et al., "Lasting cortical activation after repetitive TMS of the motor cortex," Neurology 54, pp. 956-963 (Feb. 2000).
Ziemann et al., "Modulation of Plasticity in Human Motor Cortex after Forearm Ischemic Nerve Block," The Journal of Neuroscience, vol. 18, No. 3, pp. 1115-1123 (Feb. 1998).
Oliveri et al., "Paired transcranial magnetic stimulation protocols reveal a pattern of inhibition and facilitation in the human parietal cortex," The Journal of Physiology, 529.2, pp. 461-468 (2000).
Classen, et al., "Rapid Plasticity of Human Cortical Movement Representation Induced by Practice, " The Journal of Neurophysiology, vol. 79, No. 2, pp. 1117-1123 (Feb. 1998).
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).
Gordon et al., "Parameters for direct cortical electrical stimulation in the human: histopathologic confirmation," Electroencephalography and clinical Neurophysiology, vol. 75, pp. 371-377 (1990).
Cramer, S.C. and Bastings, E.P., "Mapping clinically relevant plasticity after stroke," Neuropharmacology vol. 19, No. 5, pp. 842-851 (Apr. 2000).
Hodge, JR., C.J. and Boakye, M., "Biological Plasticity: The Future of Science in Neurosurgery," Neurosurgery, vol. 48, No. 1 (Jan. 2001).
Nitsche, M.A. and Paulus, W., "Excitability changes induced in the human motor cortex by weak transcranial direct current stimulation," The Journal of Physiology, vol. 527.3, pp. 633-639 (2000).
Rossi et al., "Effects of Repetitve Transcranial Magnetic Stimulation on Movement-related Cortical Activity in Humans," Cerebral Cortex, vol. 10, No. 8, pp. 802-808 (Aug. 2000).
Cincotta et al., "Reorganization of the motor cortex in a patient with congenital hemiparesis and mirror movements," Neurology, vol. 55, pp. 129-131 (2000).

Stefan et al., "Introduction of plasticity in the human motor cortex by paired associative stimulation," Brian, vol. 123, No. 3, pp. 575-584 (Mar. 2000).
Feys et al., "Value of somatosensory and motor evoked potentials in predicting arm recovery after a stroke," (Oct. 1999).
Turton, a. and Lemon, R.N., "The contribution of fast corticospinal input to the voluntary activation of proximal muslces in normal subjects and in stroke patients," Exp. Brian Res., vol. 129, pp. 559-572 (1999).
Martinez et al., "Motor hand recovery after stroke Prognostic yield of early transcranial magnetic stimulation," Electromyography. Clin. Neurophysiology, 39, pp. 405-410 (1999).
Saitou et al., "Cerebral Blood Volume and Oxygenation Among Poststroke Hemilplegic Patients: Effects of 13 Rehabilitation Tasks Measured by Near-Infrared Spectroscopy," Arch. Phys. Med. Rehabil., vol. 81 pp. 1348-1356.
Malenka, R.C. and Nicoll, R.A., "Long-Term Potentiation—A Decade of Progress?," Neuroscience, vol. 285, No. 5435, Issue of Sep. 17, 1999, pp. 1870-1874.
Sanes, J.N. and Donoghue, J.P., "Plasticity and Primary Motor Cortex," Annu. Rev. Neurosci. 23:393-415 (2000).
Franzini et al., "Reversal of thalamic hand syndrome by long-term motor cortex stimulation," Journal of Neurosurgery 93:873-875 (2000).
Walker-Batson et al., "Amphetamine Paired With Physical Therapy Accelerates Motor Recovery After Stroke," Stroke, vol. 26, No. 12, pp. 2254-2259 (1995).
Netz et al., "Reorganization of motor output in the non-affected hemisphere after stroke," Brain, 120, pp. 1579-1586 (1997).
Sanes, "The Relation between Human Brain Activity and Hand Movements," NeuroImage 11, pp. 370-374 (2000).
Sanes, J. and Donoghue, J.P., "Plasticity and Primary Motor Cortex," Annual Review of Neuroscience 23:393-415 (2000).
Sandkühler, "Learning and memory in pain pathways," Pain 88, pp. 113-118 (2000).
Dam et al., "Effects of Fluoxetine and Maprotiline of Functional Recovery in Poststroke Hemiplegic Pateitns Undergoing Rehabilitation Theraphy," Stroke, vol. 27, No. 7, pp. 1211-1214 (Jul. 1996).
Bel, S. and Bauer, B.L., "Dorsal Column Stimulation (DCS): Cost to Benefit Analysis," Acta Neurochirurgica, Suppl. 52, pp. 121-123 (1991).
Kopell et al., "The Continuing Evolution of Psychiatric Neurosurgery" Spectrums, vol. 5, No. 10, pp. 20-31 (Oct. 2000).
Rezai, "Neurostimulation," Neurological Research, vol. 22, No. 3 pp. 235-273 (Apr. 2000).
Turton et al., "Contralateral and ipsilateral EMG responses to transcranial magnetic stimulation during recovery of arm and hand function after stroke," Electroencephalography and Clinical Neurophysiology 101 pp. 316-328 (1996).
Bütefisch et al., "Mechanisms of use-dependent plasticity in the human motor cortex," Proc. Natl. Acad. Sci. USA, vol. 97, No. 7, pp. 3661-3665 (Mar. 2000).
Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).
Kauhanen et al., "Domans and Determinants of Quality of Life After Stroke Caused by Brian Infarction," Arch. Phys. Med. Rehabil., vol. 81, pp. 1541-1546 (Dec. 2000).
Ziemann et al., "Modulation of Plasticity in Human Motor Cortex after Forearm Ischemic Nerve Block," The Journal of Neuroscience 18(3):1115-1123 (Feb. 1998).
Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).
Cohen et al., "Studies of Neuroplasticity With Transcranial Magnetic Stimulation," The Journal of Clinical Neurophysiology, vol. 15, No. 4 (1998).
Shimizu et al., "Therapeutic efficacy of transcranial magnetic stimulation for hereditary spinocerebellar degeneration," Tohoku Journal of Experimental Medicine, 189(3):203-11 (Nov. 1999).
Liepert et al., "Treatment-Induced Cortical Reorganization After Stroke in Humans," Stroke, 31:1210-1216 (2000).

Schiff et al., "A neuromodulation strategy for rational therapy of complex brain injury states," Neurological Research, vol. 22 pp. 267-272 (Apr. 2000).
Gladstone et al., "Enhancing Recovery after Stroke with Noradrenergic Pharmacotherapy: A New Frontier?," Can J. Neurol. Sci., vol. 27, No. 2 (May 2000).
Pascual-Leone et al., "Study and Modulation of Human Cortical Excitability With Transcranial Magnetic Stimulation," Journal of Clinical Neurophysiology, vol. 15, No. 4 (1998).
Pascual-Leone et al., "Transcranial magnetic stimulation and neuroplasticity," Neurophycologia 37, pp. 207-217 (1999).
Stefan et al., "Induction of plasticity in the human motor cortex by paired associative stimulation," Brain, 123, pp. 572-584 (2000).
Canavero, S. and Paolotti, R., "Extradural Motor Cortex Stimulation for Advanced Parkinson's Disease: Case Report," *Movement Disorders* 15(1):169-171, 2000.
Benabid, A.L. et al, "Chronic electrical stimulation of ventralis intermedius nucleus of the thalamus as a treatment of movement disorders," J. Neurosurg., Apr. 1997, 86(4); 737; http://www.ncbi.nim.nih.gov, [accessed Nov. 18, 2003].
Hummel, Friedhelm et al., "Effects of non-invasive cortical stimulation on skilled motor function in chronic stroke," Brain Advance Access, Jan. 5, 2005, pp. 1-10, Brain.
International Search Report for Application No. PCT/US02/07077; Applicant: Vertis Neuroscience, Inc., Oct. 22, 2002, 7 pgs.
International Search Report for Application No. PCT/US02/32695; Applicant: Vertis Neuroscience, Inc.; Dec. 27, 2002; 9 pgs; European Patent Office.
International Search Report for Application No. PCT/US04/20786; Applicant Northstar Neuroscience, Inc., Jan. 18, 2005, 8 pgs.
International Search Report for PCT/US02/31112; Dec. 2002; Applicant: Vertis Neuroscience, Inc. (7 pgs).
International Search Report for PCT/US02/31127; Jul. 2003; Applicant: Vertis Neuroscience, Inc. (3 pgs).
International Search Report for PCT/US02/31128; Sep. 2002; Applicant: Vertis Neuroscience, Inc. (6 pgs).
International Search Report for PCT/US03/03678; Jul. 2003; Applicant: Northstar Neuroscience, Inc. (4 pgs).
International Search Report for PCT/US03/39077; May 2004; Applicant: Northstar Neuroscience, Inc. (3 pgs).
International Search Report for PCT/US03/39078; May 2004; Applicant: North Star Neuroscience, Inc. (5 pgs).
Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.
Medtronic, Inc., "Neurostimulator and Their Selection," http://www.medtronic.com/neuro/paintherapies/pain_treatment_ladder/neurostimulation/stimulators_stim_sel/neuro_stim_stim_sel.html, (2001), 6 pgs, Minneapolis, MN.
Nitsche, Michael a. et al., "Level of action of cathodal DC polarisation induced inhibition of the human motor cortex," Dec. 2, 2002, Clinical Neurophysiology 114 (2003) 600-604.
Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.
Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.
Written Opinion for PCT/US02/07077; Jul. 2003; Applicant: Vertis Neuroscience, Inc. (4 pgs).
Written Opinion for PCT US02/31112; Aug. 2003; Applicant: Vertis Neuroscience, Inc. (5 pgs).
Written Opinion for PCT/US02/31127; May 2003; Applicant: Vertis Neuroscience, Inc. (2 pgs).
Written Opinion for PCT/US02/32695; Jun. 2003; Applicant: Vertis Neuroscience, Inc. (2 pgs).
Written Opinion for PCT/US03/03678; Dec. 2003; Applicant: Northstar Neuroscience, Inc. (4 pgs).

Hartveit, E. et al., "Brain Stem Modulation of Spatial Receptive Field Properties of Single Cells in the Dorsal Lateral Geniculate Nucleus of the Cat," Journal of Neurophysiology, Oct. 1993, pp. 1644-1655, vol. 70, No. 4.

Liu, Rong-Huan et al., "Electrophysiological Properties of Mitogen-Expanded Adult Rat Spinal Cord and Subventricular Zone Neural Precursor Cells," Experimental Neurology, Mar. 1999, pp. 143-154, vol. 158.

Miyakoshi, Junji et al., "Exposure to magnetic field (5 mT at 60 Hz) does not affect cell groth and c-myc gene expression," Journal of Radiation Research, Sep. 1996, pp. 185-191, vol. 37, No. 3, The Japan radiation Research Society, Chiba, Japan.

Pearson, Helen, "Shock tactics for new neurons—Electricity may trigger nerve growth.", http://www.nature.com/nsu/010315/010315-8.html, (Mar. 14, 2001), 2 pgs, Nature News Service, Macmillan Magazines Ltd 2001.

Rodegerdts, Enno A. et al., "In Vitro Evaluation of Teratogenic Effects by Time-Varying MR Gradient Fields on Fetal Human Fibroblasts," Journal of Magnetic Resonance Imaging, (2000), pp. 150-156, vol. 12, Wiley-Liss Inc.

Ross, Philip E., "The New Physical Therapy," Red Herring, May 2001, pp. 176, 178 and 180.

Sato, Kei et al., "Growth of human cultured cells exposed to a non-homogeneous static magnetic field generated by Sm-Co magnets," Biochimica et Biophysica Acta, (1992), pp. 231-238, vol. 1136, Elsevier Science Publishers.

Van Inzen, Wouter G. et al., "Neuronal differentiation of embryonic stem cells," Biochimica et Biophysica Acta, (1996), pp. 21-26, vol. 1312, Eslevier Science.

Viktora, L. et al., "Effect of Prolonged Exposure to a Magnetic Field on the Haematopoietic Stem Cell," Physiologia Bohemoslavaca, (1976), pp. 359-364, vol. 25, Vol. 4., Institute of Haematology and Blood Transfusion, Prague.

Barr, Deborah et al., "Induction and Reversal of Long-Term Potentiation by Low-and High- Intensity Theta Pattern Stimulation," The Journal of Neuroscience, 15(7): pp. 5402-5410 (Jul. 1995).

Behrens, T. et al., "Non-invasive mapping of connection between human thalamus and cortex using diffusion imaging," Nature Neuroscience, vol. 6 No. 7, pp. 750-757 (Jul. 2003).

Brain Electrical Stimulation to Enhance Recover After Stroke. ClinicalTrials.gov. [Retrieved on Dec. 22, 2005]. Retrieved from the internet <URL http://www.clinicaltrials.gov/ct/show/NCT00085657?order=2>.

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Cytokines Web Clinical Significance. Cytokines Web, 2 pages. [Retrieved on Sep. 2, 2005]. Retrieved from the internet: <URL: <http://cmbi.bjmu.edu.cn/cmbidata/cgf/CGF_Database/cytweb/roles/index.html>>.

De Ridder, Dirk et al., "Magnetic Electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppressess specific excitatory circuits in the human motor cortex," Physiology in Press; published online on Apr. 21, 2005 as 10.1113/jphysio.2005.087288.

Ding, Yuemin et al., "Neural Plasticity After Spinal Cord Injury," Current Pharmaceutical Design vol. 11, No. 11, pp. 1441-1450, Abstract Only- 1 page (Apr. 2005).

Duncan, Pamela W. et al., "Defining post-stroke recovery: implications for design and interpretation of drug trials," Neuropharmacology vol. 39, pp. 835-841 (2000).

Fregni, Felipe et al., "Anodal transcranial Direct Current Stimulation of Prefrontal Cortex Enhances Working Memory," Experimental Brain Research vol. 166, No. 1, pp. 23-30 (Sep. 2005).

Hagemann, Georg et al., "Increased Long-Term Potentiation in the Surround of Experimentally Induced Focal Cortical Infarcrtion," Annals of Neurology, vol. 44, No. 2, pp. 255-258 (Aug. 1998).

Hayakawa, Toshiji et al., "Changes in Cerebral Oxygenation and Hemodynamics During Obstructive Sleep Apneas," Chest, vol. 109, pp. 916-921 (1996).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topolgraphy to physiological monitoring of the cortex during cortical mapping: technical case report," Surgical Neurology, vol. 64, pp. 272-275 (2005).

Huang, Ying-Zu et al., "Theta Burst Stimulation of the Human Motor Cortex," Neuron, vol. 45, pp. 201-206 (Jan. 20, 2005).

International Search Report and Written Opinion for PCT/US03/32599; Filed Oct. 15, 2003; Applicant: Northstar Neuroscience, Inc. (7 pages).

Kilgard, Michael et al., "Cortical Map Reorganization Enabled by Nucleus Basalis Activity," Science, vol. 279 pp. 1714-1717 (Mar. 13, 1998).

L-DOPA dyskinesias. BioChemistry of PD. [Retrieved on Dec. 22, 2005]. Retrieved from the internet <URL http://www.mayo.edu/fdp/pd-info/dyskinesias.htm>.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

Mansur, C.G., et al., "A sham stimulation-controlled trial of rTMS of the unaffected hemisphere in stroke patients," Neurology, vol. 64, pp. 1802-1804 (2005).

Martin et al, "Transcranial Magnetic Stimulation as a Complementary Treatment for Aphasia," Semin Speech Language, vol. 25, pp. 181-191 (2004) Abstract Only-1 page.

Meyerson, B.A. et al., "Motor Cortex Stimulation as treatment of Trigeminal Neuropathic Pain," Acta Neurochirurgica Supplementum, vol. 58, pp. 150-153 (1993).

Panchanathan, Sethuraman et al., "Rehabilitation of patients with hemispatial neglect using visual-haptic feedback in Virtual reality environment," [Retrieved on Dec. 22, 2005]. Retrieved from the internet <URL http://www.public.asu.edu/~tmcdani/publications.html>.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On WIsconsin Alumni Magazine, Summer 2003, [Retrieved on Dec. 22, 2005]. Retrieved from the internet <RUL http://www.uwalumni.com/onwisconsin/2003_summer/research.html>.

Schaefer, Pamela W. et al., "Assessing Tissue Viability with MR Diffusion and Perfusion Imaging," AJNR, 24: pp. 436-443 (Mar. 2003).

Schiene, Klasus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

SCIRun. Scientific Computing and Imaging Institute, 2 pages. [Retrieved on Jul. 24, 2005]. Retrieved from the internet: <URL: <http://software.sci.utah.edu/scirun.html>>.

Strangman, Gary et al., "A Quantitative Comparison of Simultaneous BOLD fMRI and NIRS Recordings during Functional Brain Activation," NeuroImage, vol. 17, pp. 719-731 (2002).

Strangeman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]. Retrieved from the internet <URL http://www.somanetics.net.invos.htm>.

THEORET, Hugo et al., "Exploring Pradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Toronov, Vlad et al., "Near-infrared study of fluctuations in cerebral hemodynamics during rest and motor stimulation: temporal analysis and spatial mapping," Medical Physics, vol. 27, no. 4, pp. 801-815 (Apr. 2000).

Tractography. Absolute Astronomy Reference, 2 -ages. [Retrieved on Jul. 24, 2005]. Retrieved from the internet: <URL: http://www.absoluteastronomy.com/encyclopedia/T/Tr/Tractorgraphy.htm>.

Tsubokawa, T. et al., "Chronic Motor Cortex Stimulation for the Treatment of Central Pain", Acta Neurochirurgica, Suppl. 52, pp. 137-139 (1991).

Tsubokawa, T. et al., "Treatment of Thalamic Pain by Chronic Motor Cortex Stimulation," PACE, vol. 14, pp. 131-134 (Jan. 1991).

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Yokoh, Arika et al., "Intermittent versus continuous brain retraction," Journal of Neurosurgery, vol. 58, pp. 918-923 (Jun. 1983).

Bluestone, Avraham Y. et al., "Three-dimensional optical tomography of hemodynamics in the human head," Optics Express, vol. 9, No. 6, pp. 272-286 (Sep. 10, 2001).

How Imagent™ Works. ISS Inc., 1 page [Retrieved on Oct. 14, 2005]. Retrieved from the internet: <URL http://www.iss.com/Products/imagent_fmri.html>.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent.pdf>.

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Timmermann, Lars et al., "The cerebral oscillatory network of parkinsonian resting tremor," Brain, vol. 126, pp. 199-212, (2003).

Cao, Yue et al., "Cortical Language Activation in Stroke Patients Recovering From Aphasia With Functional MRI," Stroke, vol. 30, pp. 2331-2340, Nov. 1999.

Beveridge, J. A., "Use of Exogenous Electric Current in the Treatment of Delayed Lesions in Perihperal Nerves," Plastic and Reconstructive Surger, Oct. 1988, vol. 82, No. 4, pp. 573-579.

Politis, M. J., "Mammalian Optic nerve Regeneration Following the Application of Electric Fields," The Journal of Trauma, Nov. 1988, vol. 28, No. 11, pp. 1548-1552.

Bezard et al., "Cortical Stimulation oand Epileptic Seizure: A Study of the Potential Risk in Primates," Neurosurgery, vol. 45, No. 2, Aug. 1999, 346-350.

Bindoer, J. M.D., "Functional magnetic Resonance Imaging: Language Mapping," Neurosurgery Clinics of North America, vol. 8, No. 3, Jul. 1997, pp. 383-392.

Cicnelli et al., "Transcranial magnetic stimulation revelas an interhemispheric asymmetry of cortical inhibition in focal epilepsy," Neurophysiology, vol. 11, No. 4 Mar. 20, 2000, pp. 701-707.

Cramer et al., "Use of Functional MRI to Guide Decisions in a clinical Stroke Trial," Stroke, Journal of the American Heart Association, May 2005, pp. e50-e52, American Heart Association, Dallas TX.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Fregni et al., "Antiepileptic Effects of Repetitve Transcranial Magnetic Stimulation in Ptients with Cortical Malformations: An EEG and Clinical Study," ASSFN Proceedings 2004, Stereotactic and Functional Neurosurgery, 2005, 83:57-62.

Haglund, Michael M. et al., "Optical imaging of epileptiform and functional activity in human cerebral cortex," Nature, Aug. 20, 1992, pp. 668-671, vol. 358, Nature Publishing Group.

Kelly-Spratt, K. "Transfection of PC-12 cells: a model system for primary neuronal cells," Qiagen News, Customer application article, www.qiagen.com, Issue 4, 1998, 2 pages.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Price, J. et al., "Neurotransplantation in neurodegenerative disease: a survey of relevant issues in developmental neurobiolgy," Novartis Foundation Symposium 231, 2000, pp. 148-165, Wiley, Chichester, UK.

Sioutos et al. Continuous Regional Cerebral Cortical Blood Flow Monitoring in Head-injured Patients, Neurosurgery, vol. 36, No. 5, May 1995, pp. 943-949.

The National Institutes of Helath (NIH) Consensus Development Program, "Surgery for Epilepsy," National Institutes of Health Consensos Development conference Statement, Mar. 19-21, 1990, 16 pages.

Velasco et al. "Absolute and Relative Predictor Values of Some Non-Invasive and Invasive Studies for the Outcome of Anterior Temperal Lobectormy," Science Direct, vol. 31, Issue 1, Jan.-Feb. 2000, pp. 62-74, Elsevier Science, Inc.

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recover of Motor hand Function following Hemiparetic Stroke," Abstract: Apr. 18, 2005, AANS.org, http://www.aans.org/Library/Article.aspx?ArticleId=24934, 2 pages.

U.S. Appl. No. 10/583,630, filed Jun. 20, 2006, Lozano

U.S. Appl. No. 11/254,060, filed Oct. 19, 2005, Wyler.

U.S. Appl. No. 11/254,240, filed Oct. 19, 2005, Wyler.

U.S. Appl. No. 11/255,187, filed Oct. 19, 2005, Firlik.

U.S. Appl. No. 11/344,453, filed Jan. 30, 2006, Gliner.

U.S. Appl. No. 11/518,139, filed Sep. 7, 2006, Weinand.

U.S. Appl. No. 11/583,349, filed Oct. 18, 2006, Sloan.

U.S. Appl. No. 11/683,326, filed Dec. 12, 2006, Gliner et al.

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Schulz et al., "Localization of Epileptic Auras Induced on Stimulation by Subdural Electrodes," Epilepsia, Dec. 1997, vol. 38, Issue 12, pp. 1321-1329.

Storer et al., "Microiontophoretic application of werotonin (5Ht)1B/1D agonists inhibits trigeminal cell firing in the cat," Brain, 1997, vol. 120, Issue 12, pp. 2171-2177, Oxford University Press.

Suzuki et al., "Selective Electrical Stimulationo f Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Vanderkooy et al., "Resolution Below the Least Significant Bit in Digital Systems with Dither," JAES, Mar. 1984, vol. 32, No. 3, pp. 106-113.

U.S. Appl. No. 11/697,694, filed Apr. 6, 2007, Fowler.

U.S. Appl. No. 11/697,696, filed Apr. 6, 2007, Pascual-Leone.

U.S. Appl. No. 11/697,703, filed Apr. 6, 2007, Gaw.

Barres, et al., "Proliferation of oligodendrocyte precursor cells depends on electrical activity in axons," nature; Medical Research Council Developmental Neurobiology Programme, Department of Biology, University College, London, p. 258-260, (Jan. 21, 1993).

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL http://--www.mcmaster.ca-inabis98-schallert-bury0827-two.html#introduction>.

Cheun et al., "Differentiation of a Stem Cell Line Toward a Neuronal Phenotype," Int. J. Devl. Neuroscience, vol. 9, No. 4, pp. 391-404 (1991).

Ishibashi, Tomoko et al., "Astrocytes Promote Myelination in Response to Electrical Impuses," Neuron 49, pp. 823-832, (Mar. 16, 2006).

Nudo, Randolph J., et al., "Recovery after damage to motor cortical areas," Current Opinion in Neurobiology, vol. 9, Issue 6, pp. 740-747, Dec. 1, 1999.

Robinson, Kenneth R., "The Responses of Cells to Electrical Fields: A Review," The Journal of Cell Biology, vol. 101, pp. 2023-2027 (Dec. 1985).

Tang, Cha-Min et al., "Optical Coherence Tomography of the Human Basal Ganglion,"2003 Deep Brain Stimulation Consortium Meeting, Sep. 29-30, 2003, Washington DC.

"Seizure," Wikipedia, the free encyclopedia, http://en.wikipedia.org/wiki/Seizure, internet accessed on Oct. 2, 2007, 5 pages.

"What is epilepsy? Find the definition for epilepsy and WebMD," http://dictionary.webmd.com/terms/epilepsy.xml, internet accessed on Nov. 16, 2007, 3 pages.

Australian Examiner's Report for Application No. 2003295349; Northstar Neuroscience, Inc.; Dec. 2007; 3 pgs; Australian Patent Office.

Cincotta et al., "Reorganization of the motor cortex in a patient with congential hemiparesis and mirror movements," Neurology, vol. 55, pp. 129-131, Dec. 2002.

Devinsky et al., "Clinical and electroencephalographic features of simple partial seizures," Neurology, 38, Sep. 1988, pp. 1347-1352.

Devinsky et al., "Electroencephalographic studies of simple partial seizures with subdural electrode recordings," Neurology, 39, Apr. 1989, pp. 527-533.

European Search Report for Patent Application No. 03786531.8; Northstar Neuroscienc, Inc.; May 6, 2008; 6 pgs; European Patent Office.

Kossoff et al., "Effect of an External Responsive Neurostimulator on Seizures and Electrographic Discharges during Subdural Electrode Monitoring," Epilepsia 45(12):1560-1567, Oct. 2004, Blackwell Publishing, Inc.

Lutsep et al., "Safety of Cortical Stimulation in Patients with Hemiparetic Stroke," Oasis, Online Abstract Submission and Invitation System—Program Planner, International Stroke Conference Feb. 2005, 1 pages, American Stroke Association.

Mendonca et al., "Directly applied low intensity direct electric current enhances peripheral nerve regeneration in rats," J Neurosci Methods, Oct. 30, 2003, 129(2):183-90.

Misawa et al., "Low-frequency transcranial magnetic stimulation for epilpsia partialis continua due to cortical dysplasia," Journal of the Neurological Sciences, vol. 234, Mar. 2005, pp. 37-39.

Montgomery, "Thalamic Stimulation, " Neuroscience Pathways, The Cleveland Clinic Foundation, 2 pages. (date unknown).

Motamedi et al., "Optimizing Parameters for Terminating Cortical Afterdischarges with Pulse Stimulation," Epilepsia 43(8):836-846, Aug. 2002, Blackwell Publishing, Inc.

PCT International Search Report and Written Opinion for PCT/US03/32599; Northstar Neuroscience, Inc., Dec. 28, 2004, 5 pgs; ISA/US.

Press Release: the Nobel Prize in Physiology or Medicine 1986, Nobelprize.org, http://nobelprize.org/cgi-bin/print?from=%2Fnobel_prizes%2Fmedicine%2Flaureates%2..., pp. 1-5 [internet accessed Dec. 12, 2007].

Temple, "Stem cell plasticity—building the brain of our dreams," Perspectives, Nature Reviews—Neuroscience vol. 2, Jul. 2001, pp. 513-520.

Velasco et al., "Acute and Chronic Electrical Stimulation of the Centromedian Thalamic Nucleus: Modulation of Reticulo-Cortical Systems and predictor Factors for Generalized Seizure Control," Archives of Medical Research, May-Jun. 2000, 31(3):304-315, Elsevier Science, Inc.

Velasco et al., "Electrical Stimulation for Epilepsy: Stimulation of Hippocampal Foci," Proceedings of the 13th Meeting of the World Society for Stereotactic and Functional Neurosurgery, Sep. 11-14, 2001, Stereotactic and Functional Neurosurgery, vol. 77, No. 1-4, 2001, pp. 223-227.

Velasco et al., "Subacute and Chronic Electrical Stimulation of the Hippocampus on Intractable Temporal Lobe Seizures: Preliminary Report," Archives of Medical Research, May-Jun. 2000, 31(3):316-28, Elsevier Science.

Velasco et al., "Subacute Electrical Stimulation of the Hippocampus Blocks Intractable Temporal Lobe Seizures and Paroxysmal EEG Activities," Epilepsia, Feb., 2000, 41(2):158-169, Lippincott Williams & Wilkins, Philadelphia.

Yamamoto et al., "Low-frequency Electric Cortical Stimulation Has an Inhibotory Effect on Epileptic Focus in Mesial temporal Lobe Epilepsy," Epilepsia, vol. 43, No. 5, May 2002, pp. 291-295, Blackwell Publishing, Inc.

* cited by examiner

NEURAL STIMULATION SYSTEM AND METHOD RESPONSIVE TO COLLATERAL NEURAL ACTIVITY

CROSS-REFERENCE TO RELATED APPLICATION(S)

This application is a Continuation-in-Part of U.S. application Ser. No. 09/978,134, entitled "Systems and Methods for Automatically Optimizing Stimulus Parameters and Electrode Configurations for Neuro-Stimulators," filed Oct. 15, 2001, now U.S. Pat. No. 7,305,268 which is incorporated herein by reference.

TECHNICAL FIELD

The present disclosure is related to systems and methods for detecting and responding to collateral neural activity that may arise in association with or as a result of stimulation applied to a region of the cortex or other area of the brain.

BACKGROUND

A wide variety of mental and physical processes are controlled or influenced by neural activity in particular regions of the brain. For example, the neural-functions in some areas of the brain (i.e., the sensory or motor cortices) are organized according to physical or cognitive functions. There are also several other areas of the brain that appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory, and intellect.

Many problems or abnormalities with body functions can be caused by damage, disease and/or disorders in the brain. Effectively treating such abnormalities may be very difficult. For example, a stroke is a very common condition that damages the brain. Strokes are generally caused by emboli (e.g., obstruction of a vessel), hemorrhages (e.g., rupture of a vessel), or thrombi (e.g., clotting) in the vascular system of a specific region of the brain, which in turn generally cause a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus drug treatment. For most patients, however, such treatments are not sufficient, and little can be done to improve the function of an affected body part beyond the limited recovery that generally occurs naturally without intervention.

The neural activity in the brain can be influenced by electrical energy that is supplied from a waveform generator or other type of device. Various patient perceptions and/or neural functions can thus be promoted or disrupted by applying an electrical current to the cortex or other region of the brain. As a result, researchers have attempted to treat various neurological conditions using electrical or magnetic stimulation signals to control or affect brain functions.

Neural activity is governed by electrical impulses or "action potentials" generated in and propagated by neurons. While in a quiescent state, a neuron is negatively polarized, and exhibits a resting membrane potential that is typically between −70 and −60 mV. Through electrical or chemical connections known as synapses, any given neuron receives from other neurons excitatory and inhibitory input signals or stimuli. A neuron integrates the excitatory and inhibitory input signals it receives, and generates or fires a series of action potentials in the event that the integration exceeds a threshold potential. A neural firing threshold may be, for example, approximately −55 mV. Action potentials propagate to the neuron's synapses, where they are conveyed to other neurons to which the neuron is synaptically connected.

A neural stimulation signal may comprise a series or train of electrical or magnetic pulses that deliver an energy dose to neurons within a target neural population. The stimulation signal may be defined or described in accordance with stimulation signal parameters including pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials. Neural stimulation that elicits or induces action potentials in a functionally significant proportion of the neural population to which the stimulation is applied is referred to as suprathreshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself fails to trigger or activate such functions. Supra-threshold neural stimulation can induce various types of measurable or monitorable responses in a patient. For example, supra-threshold stimulation applied to a patient's motor cortex can induce muscle fiber contractions.

While electrical or magnetic stimulation of neural tissue may be directed toward producing an intended type of neural activity, such stimulation may result in unintended collateral neural activity. In particular, neural stimulation for treating a condition can induce seizure activity or other types of collateral neural activity. It will be appreciated that such collateral neural activity is undesirable and/or inconvenient in a neural stimulation situation.

Seizure activity may originate at a seizure focus, which is typically a collection of neurons (e.g., on the order of 1000 neurons) exhibiting a characteristic type of synchronous firing activity. In particular, each neuron within a seizure focus exhibits a firing response known as a paroxysmal depolarizing shift (PDS). The PDS is a large magnitude, long duration depolarization that triggers a neuron to fire a train or burst of action potentials. Properly functioning feedback and/or feedforward inhibitory signaling mechanisms cause afterhyperpolarization through which the neuron's membrane potential returns to a hyperpolarized state below its firing threshold. Following afterhyperpolarization, the neuron may undergo another PDS.

Afterhyperpolarization limits the duration of the PDS, thereby helping to ensure that synchronous neural firing activity remains localized to the seizure focus. Inhibitory feedback signaling provided by neurons surrounding a seizure focus, commonly referred to as "surround inhibition," is particularly important in constraining seizure activity to the seizure focus. In the event that inhibitory signaling mechanisms fail and/or are unable to overcome or counter PDS activity, neurons within the seizure focus recruit other neurons to which they are synaptically coupled into their synchronous firing pattern. As a result, synchronous firing activity spreads beyond the seizure focus to other areas of the brain. This can lead to a cascade effect in which seizure activity becomes increasingly widespread, and accompanying clinical manifestations become increasingly significant.

In view of the foregoing, it may be important to detect and/or respond to seizure activity. Various systems and/or devices directed toward treating neurological conditions exist, including those capable of detecting and responding to particular types of neurological events. For example, some neural stimulators attempt to treat involuntary motion disorders such as Parkinson's disease by applying stimulation signals to the thalamus or other area of a patient's brain. As another example, U.S. Pat. No. 6,134,474 describes an implantable device capable of detecting a neurological event, such as seizure activity, and generating a responsive electrical signal intended to terminate the detected event. Additionally, European Patent Application Publication EP1145736 describes an implantable device capable of detecting electrical activity in the brain; applying a nonresponsive signal to reduce the likelihood of a seizure occurring; and applying a responsive signal in the event that epileptiform activity is detected.

Unfortunately, present neural stimulation systems and methods fail to automatically detect and/or respond to seizure activity or other collateral neural activity induced in association with and/or as a result of neural stimulation procedures directed toward purposes other than epileptic seizure management. In particular, conventional neural stimulation systems fail to automatically detect seizure activity induced by neural stimulation procedures directed toward patient neural function rehabilitation and/or enhancement, or modulation of patient sensory perceptions.

DETAILED DESCRIPTION

The following disclosure describes a system and method for detecting and responding to collateral neural activity that may arise in association with and/or as a result of a neural stimulation procedure. In the context of the present invention, a neural stimulation procedure may involve the application of stimuli to one or more target neural populations within a patient, and may be directed toward rehabilitating, restoring, and/or enhancing one or more neural functions in the patient by facilitating and/or effectuating a neuroplastic change or reorganization. A neural stimulation procedure may alternatively or additionally be directed toward modulating or ameliorating a patient sensory perception such as pain, or affecting a neurological condition that is present on a continuous or essentially continuous basis in the absence of the applied stimuli. Collateral neural activity may comprise seizure activity, migraine activity, and/or essentially any other type of neural activity that may be undesirable, unwanted, unintended, and/or counterproductive relative to an intended or desired neural activity or outcome associated with the neural stimulation procedure.

Figure 1:
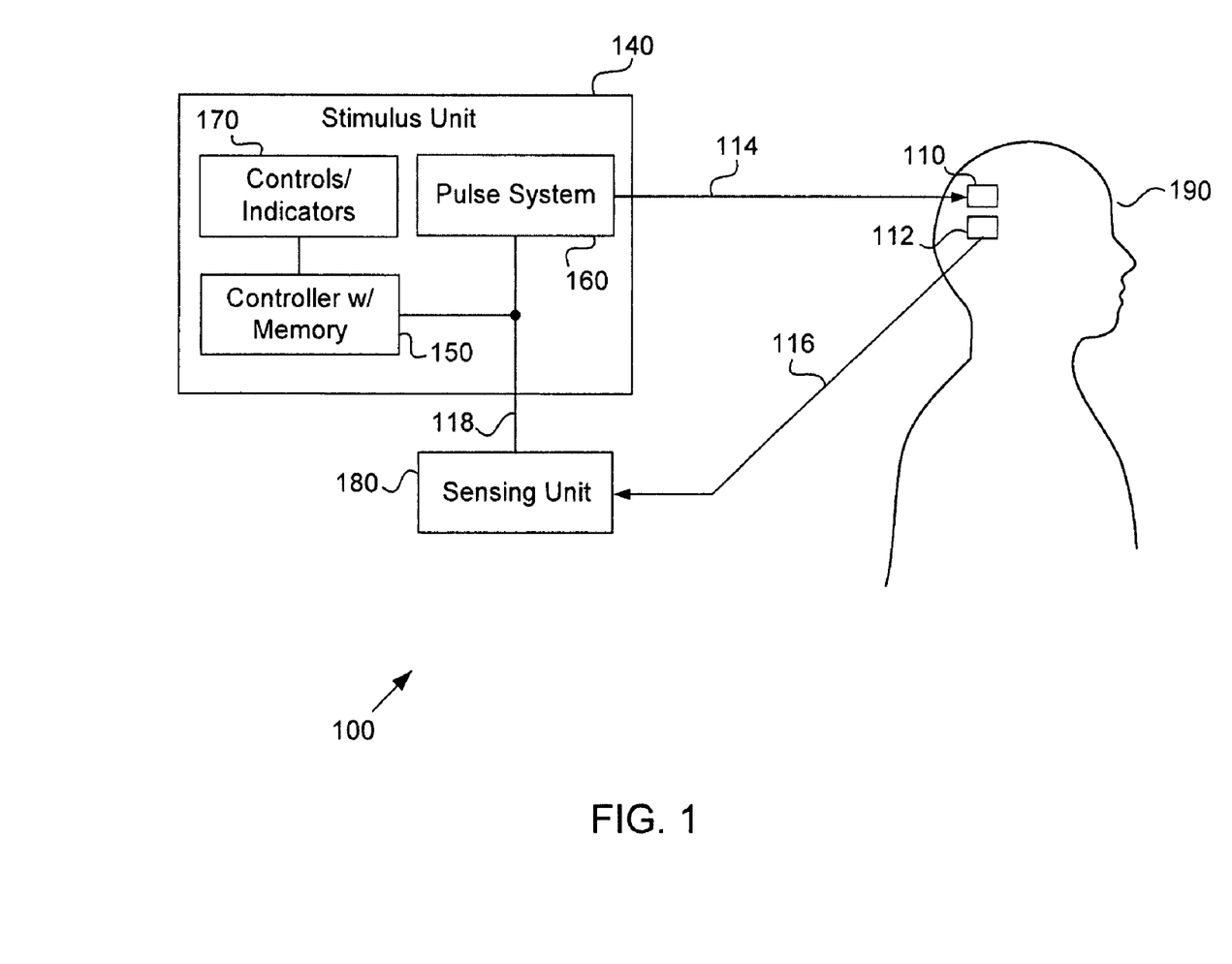
FIG. 1 is a schematic illustration of a neural stimulation system responsive to specific neural activity according to an embodiment of the invention.

FIG. 1 is a schematic illustration of a neural stimulation system 100 for detecting and responding to collateral neural activity according to an embodiment of the invention. In one embodiment, the system 100 comprises a stimulus unit 140 configured to deliver stimulation signals to a patient 190 using a stimulation interface 110. The system 100 may additionally comprise a sensing unit 180 configured to identify or detect parameters associated with collateral neural activity in the patient 190 using a monitoring interface 112. The sensing unit 180 is configured to communicate with the stimulus unit 140 upon detection of collateral neural activity and/or periodically throughout a stimulation procedure. The stimulus unit 140 may be coupled to the stimulation interface 110 by a first link 114; the monitoring interface 112 may be coupled to the sensing unit 180 by a second link 116; and the sensing unit 180 may be coupled to the stimulus unit 140 by a third link 118, where one or more of such links 114, 116, 118 may be wire-based or wireless.

The stimulus unit 140 generates and outputs stimulation signals. As considered herein, stimulation signals may include treatment signals and/or response signals. Treatment signals may comprise electrical and/or magnetic stimuli applied to one or more target neural populations and directed toward treating and/or rehabilitating one or more neurological conditions. The treatment signals may also affect or influence particular types of neurological activity. In general, treatment signals may be directed toward affecting or altering one or more neurological conditions that exist within the patient 190 on a continuous, essentially continuous, or nearly continuous basis (i.e., non-intermittent or essentially non-intermittent through potentially cyclical) in the absence of the treatment signal. Treatment signals may be directed toward facilitating and/or effectuating neuroplasticity in the patient 190, for example, in a manner described in U.S. patent application Ser. No. 09/978,134, which is incorporated herein by reference. Treatment signals may alternatively or additionally be directed toward affecting or modulating a patient sensation such as pain; or eliminating or ameliorating the effects of neurodegenerative disorders, for example, involuntary movements and/or other symptoms associated with Parkinson's disease.

In general, response signals may comprise electrical, magnetic, and/or other (e.g., sonic or vibratory) stimuli directed toward disrupting, desynchronizing, abating, and/or eliminating collateral neural activity arising in association with or as a result of the application of treatment signals to the patient 190. Depending upon their nature, response signals may be applied proximate or directly to one or more target neural populations and/or particular patient sensory systems or body locations. The description that follows considers electromagnetic response signals; however, the present invention may employ other or additional types of response signals in a manner understood by those skilled in the art.

Figure 2:
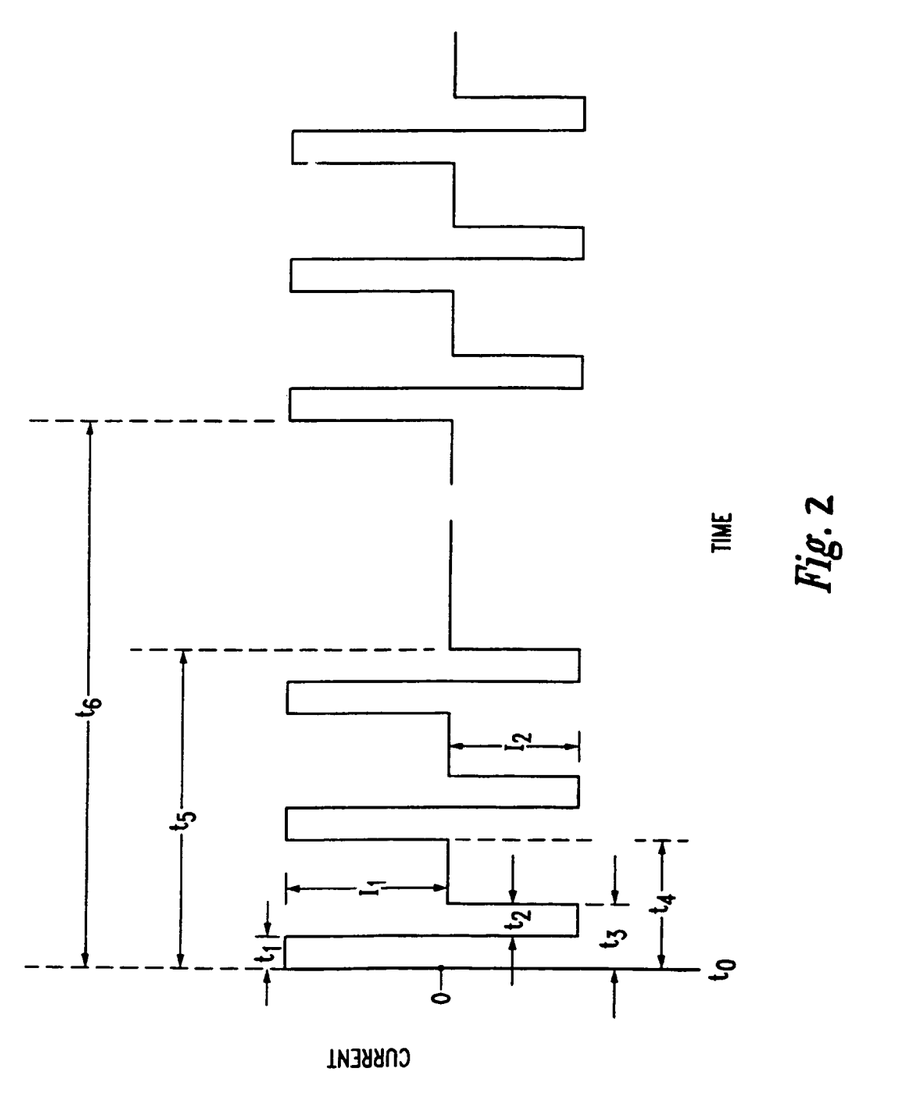
FIG. 2 is a graph illustrating several parameters that may describe or characterize a stimulation signal.

FIG. 2 is a graph illustrating several parameters that may define, describe, or characterize stimulation signals. A stimulus start time $t_0$ defines an initial point at which a stimulation signal is applied to the stimulation interface 110. In one embodiment, the stimulation signal may be a biphasic waveform comprising a series of biphasic pulses, and which may be defined, characterized, or described by parameters including a pulse width $t_1$ for a first pulse phase; a pulse width $t_2$ for a second pulse phase; and a pulse width $t_3$ for a single biphasic pulse. The parameters can also include a stimulus repetition rate $1/t_4$ corresponding to a pulse repetition frequency; a stimulus pulse duty cycle equal to $t_3$ divided by $t_4$; a stimulus burst time $t_5$ that defines a number of pulses in a pulse train; and/or a pulse train repetition rate $1/t_6$ that defines a stimulus burst frequency. Other parameters include a peak current intensity $I_1$ for the first pulse phase and a peak current intensity $I_2$ for the second pulse phase. Those skilled in the art will understand that pulse intensity or amplitude may decay during one or both pulse phases, and a pulse may be a charge-balanced waveform. Those skilled in the art will further understand that in an alternate embodiment, pulses can be monophasic or polyphasic. Additional stimulation parameters may include applying the stimulation to selected configurations of the stimulation interface 110 for any given stimulation signal and/or time.

In one embodiment, the stimulus unit 140 comprises a controller 150, a pulse system 160, and a set of controls/indicators 170. The controller 150 may include a processor, a memory, and a programmable computer medium. The controller 150 may be implemented as a computer or microcontroller, and the programmable medium can be hardware and/or memory resident software that performs, directs, and/or facilitates neural stimulation procedures in accordance with the present invention. The controls/indicators 170 can include a graphic user interface, an input/output device, and/or other types of interface elements for exchanging commands and/or output with the controller 150.

The pulse system 160 selectively generates stimulation signals and sends, directs, or delivers such stimuli to the stimulation interface 110. The pulse system 160 may be implanted into the patient 190, in a manner described in U.S. application Ser. No. 09/802,808 incorporated herein by reference. Alternatively, the pulse system 160 may be an external unit capable of delivering stimulation signals to the stimulation interface 110 using RF energy, electromagnetism, or wire terminals exposed on the patient's scalp. The stimulation interface 110 may comprise one or more stimulus delivery devices configured to apply treatment signals and/or response signals to the patient 190. The stimulation interface 110 may comprise a type of neural-stimulation device described in U.S. application Ser. No. 09/802,808.

In one embodiment, the pulse system 160 is a component of a Transcranial Magnetic Stimulation (TMS) device that delivers magnetic stimulation signals to a patient 190. The stimulation interface 110 in this embodiment may comprise an electromagnetic coil arrangement in a manner understood by those skilled in the art. In another embodiment, the pulse system 160 forms a portion of an electrical stimulation device. The stimulation interface 110 of this embodiment may comprise an electrode arrangement or configuration capable of delivering electrical stimulation signals to the patient 190. In such an embodiment, the stimulation interface 110 may be implanted into the patient 190 to provide cortical stimulation, deep brain stimulation, and/or other types of neural stimulation.

Various portions or elements of the stimulation interface 110 may be configured to deliver treatment signals only, response signals only, or either treatment or response signals. One or more portions of the stimulation interface 110 may reside upon or proximate to one or more target neural populations in and/or through which a) neuroplasticity may be occurring and/or may be expected to occur; and/or b) a patient sensation such as pain may be modulated or influenced.

Figure 3A:
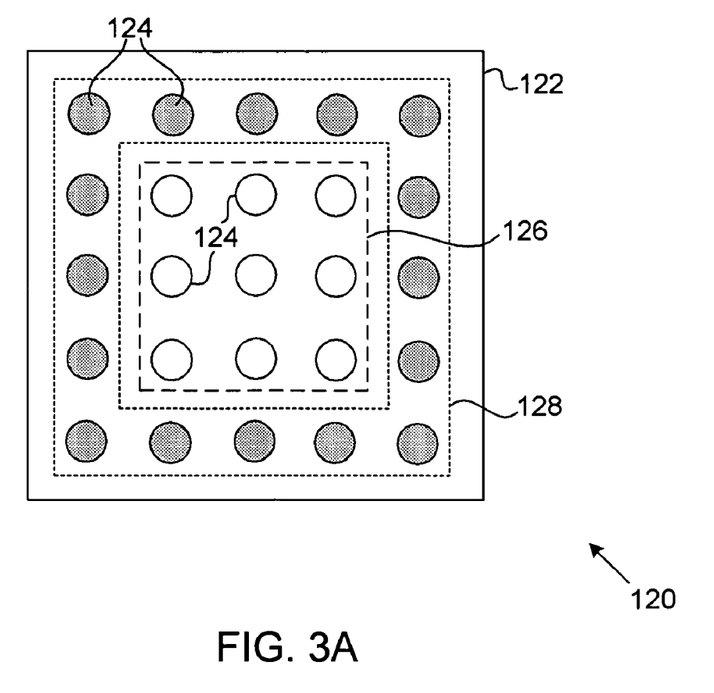
FIG. 3A is a plan view of a grid electrode configured as a stimulation interface according to an embodiment of the invention.

FIG. 3A is a plan view of an exemplary grid electrode 120 capable of implementing one or more portions of a stimulation interface 110 according to an embodiment of the invention. The grid electrode 120 comprises a support member or substrate 122 that carries a plurality of electrical contacts 124. Those skilled in the art will understand that the number of contacts 124 may vary in accordance with embodiment details. The grid electrode 120 further comprises a set of leads (not shown) that couple the contacts 124 to the pulse system 160 in a manner understood by those skilled in the art. A grid electrode 120 of the type shown in FIG. 3A is available from AdTech Medical Instrument Corporation of Racine, Wis. (www.adtechmedical.com).

The contacts 124 can be divided so that one group of contacts 124 delivers treatment signals while another group of contacts 124 delivers response signals. For example, a central contact group 126 may deliver treatment signals to a target neural population while an outer contact group 128 may deliver response signals in a manner that may enhance or promote surround inhibition. In such an embodiment, response signals may be delivered in a time-shared or a concurrent manner relative to treatment signal delivery. Alternatively, the grid electrode 120 may be configured to deliver treatment signals or response signals to all contacts 124 in a time-shared manner, or configured to deliver treatment signals only or response signals only.

The sensing unit 180 comprises a system, device, or apparatus configured to detect or identify collateral neural activity or parameters of such activity that occur in association with and/or as a result of a neural stimulation procedure. The sensing unit 180 may include a processor, a memory, and a programmable computer medium. The programmable medium of the sensing unit 180 can comprise hardware and/or software capable of analyzing signals corresponding to neural activity and determining whether collateral neural activity or evidence of such activity exists. The sensing unit 180 may communicate with the stimulus unit 140 upon detecting collateral neural activity so that the stimulus unit 140 may respond to the sensing unit 180. The sensing unit 180 may monitor for collateral neural activity or evidence of such activity on a periodic or continuous basis. The sensing unit 180, for example, can operate under the direction of or in cooperation with the controller 150. Communication between the stimulus unit 140 and the sensing unit 180 may occur through the third link 118. Such communication may involve the exchange of operational parameters, synchronization information, status information, and/or information associated with the detection of collateral neural activity.

The sensing unit 180 may receive from the monitoring interface 112 one or more types of physiological signals and/or physiological correlate signals useful for indicating the presence of collateral neural activity. In general, a meaningful, significant and/or sustained change in a physiological or physiological correlate signal relative to the signal's normal or background behavior can indicate the onset and/or occurrence of collateral neural activity. The sensing unit 180 may comprise hardware and/or software that performs signal filtering, processing, and/or analysis operations. Depending upon the nature of the physiological and/or physiological correlate signals under consideration, the sensing unit 180 and/or the monitoring interface 112 may exhibit various embodiments.

The monitoring interface 112 can have several embodiments. For example, one or more portions of the monitoring interface 112 may be oriented or positioned relative or proximate to a set of target neural populations to which a neural stimulation procedure is directed so that the monitoring interface 112 may detect or receive signals corresponding or related to such neural populations. Alternatively or additionally, one or more portions of the monitoring interface 112 may be oriented or positioned within or upon the patient's body to detect one or more types of patient responses correlated to neural activity.

In one embodiment, the sensing unit 180 comprises an electroencephalogram (EEG) monitoring and/or analysis device and the monitoring interface 112 comprises one or more surface, cortical, and/or subcortical electrodes, electrode arrays, and/or electrical probes capable of receiving or detecting EEG signals. The sensing unit 180 may analyze EEG signals received from the monitoring interface 112 and determine whether collateral neural activity or evidence of such activity exists. Those skilled in the art will recognize that particular types of EEG activity, such as interictal spikes and/or energy spectrum shifts, may be indicative of seizure activity.

In addition to EEG signals, other types of physiological signals and/or physiological correlate signals may be useful for providing evidence of collateral neural activity. For example, signals corresponding to cerebral blood flow (CBF) may be used to indicate the onset or occurrence of seizure activity, as described by M. E. Weinand et al. in an article entitled "Cerebral blood flow and temporal lobe epileptogenicity" (J. Neurosurg. 1997 Feb; 86(2): 226-32). In one embodiment, the monitoring unit 112 may comprise a CBF monitor, which may include a set of electrodes, a thermistor, and/or a thermal diffusion probe; a set of near infrared sources and sensors; a set of piezoelectric ultrasonic emitters and sensors (to facilitate, for example, transit time measurements); and/or one or more other types of CBF monitoring devices. In such an embodiment, the sensing unit 180 may comprise a CBF signal analysis system or device. In a related alternate embodiment, the monitoring unit 112 may comprise a neural tissue oxygenation monitor, and the sensing unit 180 may correspondingly comprise a neural tissue oxygenation analysis system or device.

Particular types of muscle fiber activity may also be indicative of collateral neural activity (e.g., extremely rapid muscle fiber contractions, particularly when sustained). In one embodiment, the sensing unit 180 comprises an electromyography (EMG) device configured to detect, monitor, and/or analyze motor evoked potentials (MEPs) associated with muscle fiber innervation, in a manner understood by those skilled in the art. The monitoring interface 112 correspondingly comprises a set of surface, percutaneous, and/or implanted electrodes or probes that may be positioned or configured to measure electrical activity associated with the innervation of one or more muscles and/or muscle groups. In another embodiment, the sensing unit 180 comprises a motion analysis system and the monitoring interface 112 comprises a set of motion detectors, strain gauges, and/or accelerometers configured to detect or monitor one or more types of patient movements. The sensing unit 180 may analyze motion signals received from the monitoring interface 112 and determine whether patient motions under consideration are indicative of seizure activity.

In other embodiments, the sensing unit 180 and monitoring interface 112 may comprise one or more types of neural imaging systems, such as a functional Magnetic Resonance Imaging (fMRI) system, a Positron Emission Tomography (PET) system, and/or a Magnetoencephalography (MEG) system. In general, the sensing unit 180 and/or the monitoring interface 112 may be configured to receive, detect, monitor, measure, and/or analyze one or more types of signals useful of indicating the presence of collateral neural activity.

The stimulation interface 110 and the monitoring interface 112 may be implemented as devices and/or modules that reside upon physically separate substrates or carriers positioned within and/or upon the patient 190. Alternatively or additionally, one or more portions of such interfaces 110, 112 may be implemented together upon a single implantable carrier or substrate.

Figure 3B:
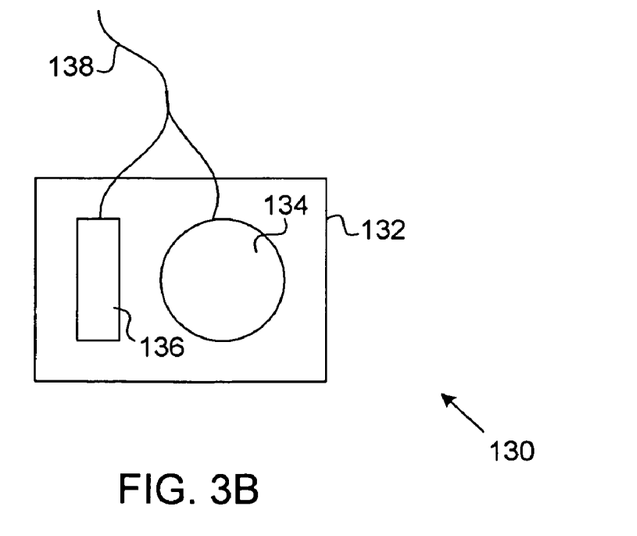
FIG. 3B is a plan view of an implantable stimulation and monitoring interface configured for stimulating a target neural population and detecting signals corresponding to specific neural activity according to an embodiment of the invention.

FIG. 3B is a plan view of an implantable stimulation and monitoring interface 130 configured for stimulating a target neural population and detecting signals corresponding to neural activity according to an embodiment of the invention. In one embodiment, the stimulation and monitoring interface 130 comprises a support member 132 carrying a stimulating element 134 and a monitoring element 136. The stimulating element 134 may comprise one or more electrodes organized in accordance with a particular pattern, and the monitoring element 126 may comprise a set of electrodes and/or a CBF monitoring device positioned proximate or adjacent to the stimulating element 134. A set of leads 138 may couple the stimulating element 134 and the monitoring element 136 to the stimulus unit 140 and the sensing unit 180, respectively. A stimulation and monitoring interface 120 may be positioned or oriented within a patient 190 such that a stimulating element 124 can deliver or apply stimulation signals to one or more particular target neural populations, and the monitoring element 126 can detect signals indicative of neural activity associated with the targeted neural populations.

As previously indicated, one or more portions of the monitoring interface 112 may comprise an electrode arrangement, which may include a grid electrode 120 of the type shown in FIG. 3A, a deep brain electrode, and/or one or more other electrode types. As a result, a stimulation and monitoring interface 130 may comprise a grid electrode 120 of the type shown in FIG. 3A. In such an embodiment, particular contacts 124 within the grid electrode 120 may be designated for neural activity monitoring and other contacts 124 may be configured to deliver treatment and/or response signals.

Depending upon the nature of the monitoring interface 112, the delivery of stimulation signals to a target neural population may interfere with the detection of signals corresponding to neural activity. As a result, the controller 150 and/or the pulse system 160 may periodically interrupt a neural stimulation procedure, such that during stimulation procedure interruptions, the sensing unit 180 may analyze signals received from the monitoring interface 112 relative to collateral neural activity. Outside of such interruptions, the sensing unit 180 may be prevented from receiving or processing signals received from the monitoring interface 112. Alternatively, the sensing unit 180 may compensate for the presence of stimulation signals, for example, through signal subtraction and/or other compensation operations, to facilitate detection of collateral neural activity or evidence of collateral neural activity simultaneous with the delivery of stimulation signals to a target neural population.

In embodiments in which a neural stimulation procedure is periodically interrupted to facilitate detection of collateral neural activity or evidence of such activity, the stimulation and monitoring interface 120 may be implemented using a single electrode arrangement or configuration in which any given electrode element used to deliver stimulation signals during the neural stimulation procedure may also be used to detect neural activity during a neural stimulation procedure interruption. Thus, the stimulation interface 110 and the monitoring interface 112 may physically be one and the same.

One or more portions of the controller 150, the pulse system 160, the stimulation interface 110, monitoring interface 112, and/or the sensing unit 180 can be integrated into a single implantable stimulation delivery, monitoring, and/or management apparatus in a manner identical analogous or similar to the devices described in U.S. application Ser. No. 09/802,808. Such an integrated apparatus may be configured for implantation into a patient's skull so that the stimulation interface 110 and/or the monitoring interface 112 can contact the patient's dura matter or pia matter in one or more cortical regions. An integrated apparatus of this type can have an internal power source that can be implanted into the patient 190, and/or an external power source coupled to the pulse system 160 via electromagnetic coupling or a direct connection.

Figure 4:
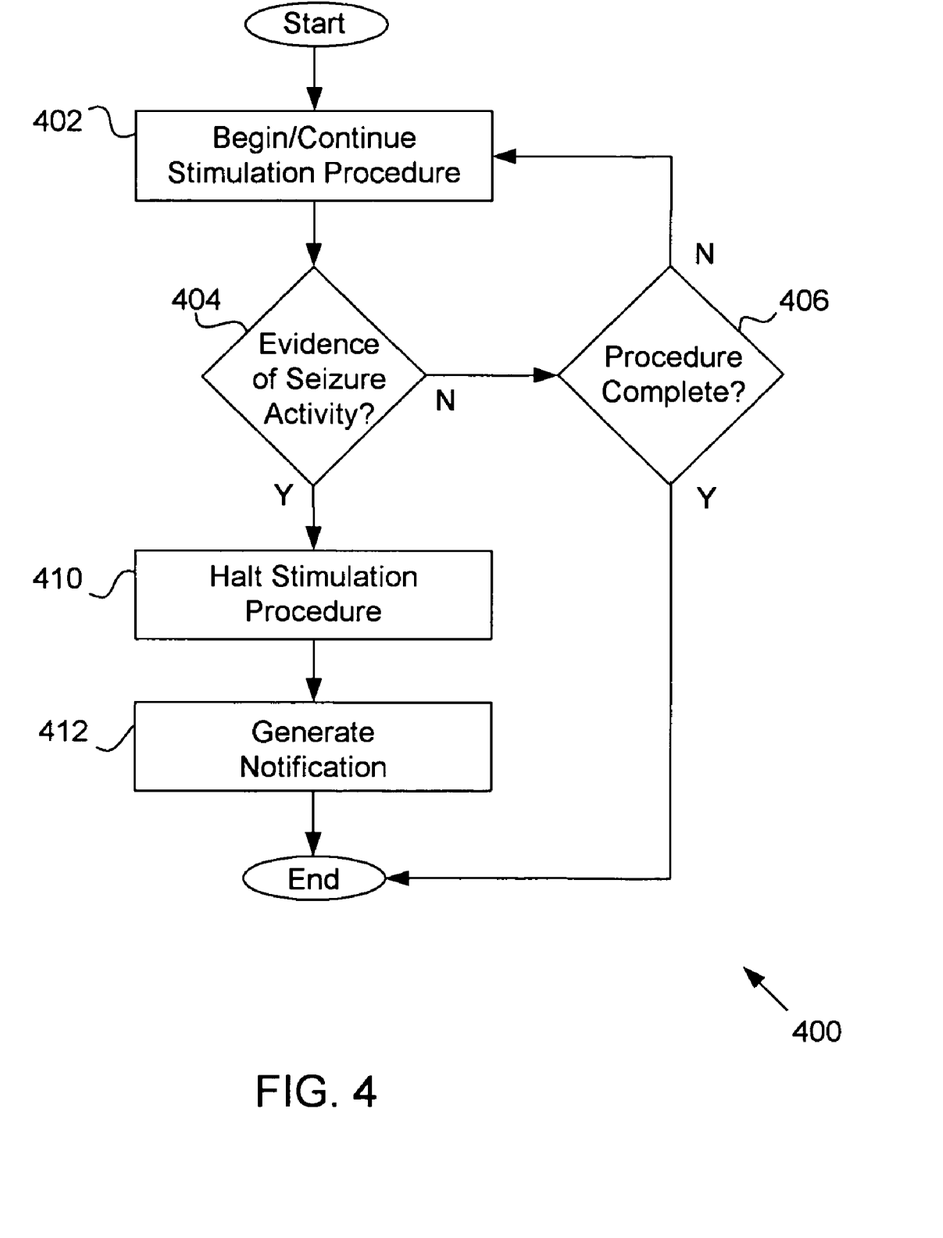
FIG. 4 is a flowchart of a neural stimulation process responsive to specific neural activity according to an embodiment of the invention.

FIG. 4 is a flowchart of a neural stimulation process 400 responsive to collateral neural activity according to an embodiment of the invention. In one embodiment, the process 400 begins with a stimulation operation 402 by initiating or continuing a neural stimulation procedure in which stimulation signals are delivered to one or more target neural populations within a patient 190 in accordance with a given set of stimulation signal parameters. After initiating the stimulation operation 402, the process 400 also includes a detection query 404 that determines whether collateral neural activity or evidence of such activity exists. The detection query 404 may be performed in a simultaneous or sequential manner relative to the stimulation operation 402. If collateral neural activity or evidence thereof does not exist, the process 400 continues with a termination query 406 that decides whether the neural stimulation procedure is complete. If the process is not complete, the process 400 returns to the stimulation operation 402; otherwise, if the process 400 is complete, it is terminated. If the detection query 404 the process 400 determines that collateral neural activity exists, the process 400 halts the neural stimulation procedure in a termination operation 410, and generates and/or issues a notification signal indicative of such activity in a notification procedure 412. Following the notification procedure 412, the process 400 ends.

Figure 5:
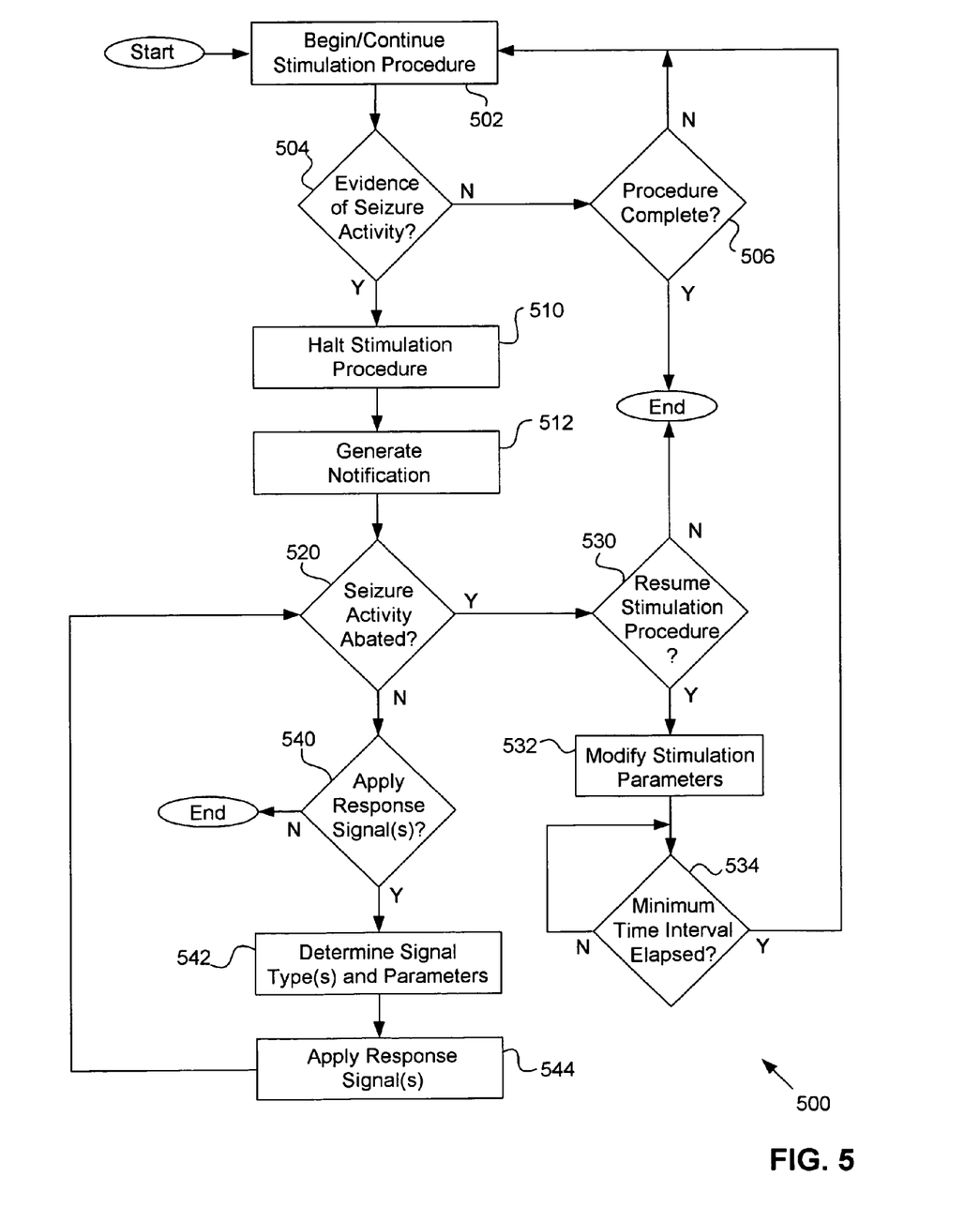
FIG. 5 is a flowchart of a neural stimulation process responsive to specific neural activity according to another embodiment of the invention.

FIG. 5 is a flowchart of a neural stimulation process 500 responsive to collateral neural activity according to another embodiment of the invention. In one embodiment, the process 500 begins with a stimulation operation 502 by initiating or continuing a neural stimulation procedure in which stimulation signals are delivered to one or more target neural populations within a patient 190 in accordance with a first set of stimulation signal parameters. Next, the process 500 includes a detection query 504 that determines whether collateral neural activity or evidence thereof exists. If not, the process 500 proceeds to a termination query 506 to determine whether the neural stimulation procedure is complete. If the neural stimulation procedure is not complete, the process 500 returns to the stimulation procedure 502; otherwise, the stimulation process 500 is terminated.

If collateral neural activity or evidence of such activity exists, the process 500 includes a termination operation 510 that halts the neural stimulation procedure and a notification procedure 512 that generates and/or issues a notification signal indicative of such activity. The stimulation process 500 proceeds to a collateral activity query 520 that subsequently determines whether the collateral neural activity has been abated or eliminated. If so, the process 500 proceeds to a query 530 that determines whether to resume the neural stimulation procedure. Such a determination may be based upon, for example, an elapsed time between initiation of a neural stimulation procedure and detection of collateral neural activity; stored information characterizing and/or specifying frequency and/or history information associated with detection of collateral neural activity in the patient 190 undergoing the neural stimulation procedure; an authorization signal received from a doctor or therapist through the controls/indicators 170; and/or other information.

If resumption of the neural stimulation procedure is to occur, the process 500 continues with a modification operation 532 in which one or more stimulation signal parameters may be modified. Such a modification may involve changing (e.g., decreasing) a stimulation current level or intensity; changing (e.g., increasing) a stimulation signal pulse repetition frequency; and/or modifying one or more other parameters shown in FIG. 2. Following the modification operation 532, the process 500 includes time query 534 to determine whether a minimum time interval has elapsed. The time query 534 may provide a quiescent period during which the patient's neural activity becomes predominantly normal and/or representative of an acceptable baseline condition. If a minimum time interval has not elapsed, the process 500 remains at the time query 534; otherwise, the process 500 returns to the stimulation operation 502.

If the collateral activity query 520 determines that collateral neural activity has not been abated, the process 500 proceeds with a response query 540 that determines whether to apply to the patient 190 one or more response signals directed toward abating or terminating the collateral neural activity. If not, the process 500 ends. Otherwise, the process 500 proceeds with a signal selection procedure 542 that determines one or more appropriate response signal types and corresponding signal parameters, and a response procedure 544 that applies one or more response signals to the patient 190. Response signals may include one or more neural stimulation and/or other types of signals applied to the patient 190 through the stimulation interface 110. Following the response procedure 544, the process 500 returns to the stimulation operation 520.

As previously indicated, a neural stimulation procedure in accordance with the present invention may facilitate and/or effectuate neuroplastic change or reorganization within a patient 190, which in turn may rehabilitate, restore, and/or enhance one or more patient neural functions and/or behaviors. To facilitate and/or effectuate neuroplasticity, a neural stimulation procedure may be performed cooperatively with a behavioral therapy, such as described in U.S. application Ser. No. 90/802,808. A behavioral therapy may encompass, for example, physical therapy, cognitive therapy, and/or a variety of behavioral tasks.

Figure 6:
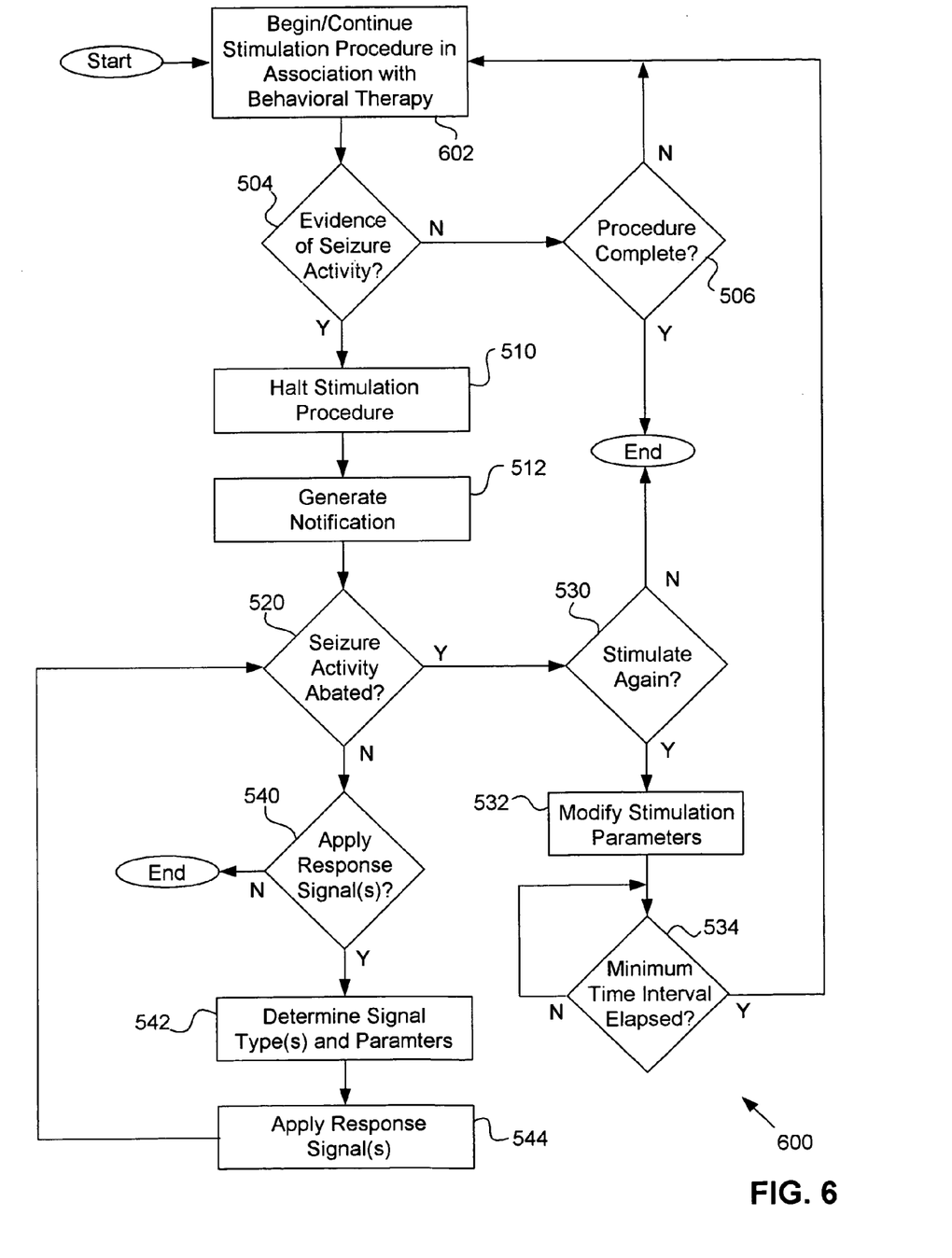
FIG. 6 is a flowchart of a neural stimulation process responsive to specific neural activity according to another embodiment of the invention.

FIG. 6 is a flowchart of a neural stimulation process 600 responsive to collateral neural activity according to another embodiment of the invention. Relative to FIG. 5, like reference numbers indicate like steps. In one embodiment, the process 600 begins with a stimulation operation 602 by initiating or continuing a neural stimulation procedure in conjunction or association with a behavioral therapy. During the stimulation operation 602, stimulation signals are delivered to one or more target neural populations within a patient 190 in accordance with a first set of stimulation signal parameters. Following the stimulation operation 602, other steps within the process 600 may proceed in manners described above with reference to FIG. 5.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A neural stimulation method, comprising:
   applying a first electrical stimulation signal to a target neural population within a patient, the first electrical stimulation signal directed towards treating pain or neurodegenerative disorders;
   determining whether counterproductive collateral neural activity exists, the counterproductive collateral neural activity being induced by the first electrical stimulation signal and including at least one of seizure activity and migraine activity; and
   responding to the counterproductive collateral neural activity when it is determined to exist such that the counterproductive collateral neural activity is inhibited.

2. The method of claim 1 wherein the neurodegenerative disorder comprises involuntary movements.

3. The method of claim 1 wherein the neurodegenerative disorder comprises Parkinson's disorder.

4. The method of claim 1 wherein the neurodegenerative disorder comprises symptoms associated with Parkinson's disorder.

5. The method of claim 1, wherein responding to the collateral neural activity comprises discontinuing application of the first electrical stimulation signal.

6. The method of claim 1, wherein responding to the collateral neural activity comprises applying a second stimulation signal to the patient.

7. The method of claim 6, wherein the second stimulation signal is applied to the target neural population and/or a neural population adjacent to a portion of the target neural population.

8. The method of claim 1, wherein determining whether collateral neural activity exists comprises monitoring an electrophysiological signal and/or a patient behavior.

9. The method of claim 1, wherein determining whether collateral neural activity exists comprises monitoring an EEG signal, a cerebral bloodflow signal, an EMG signal, an accelerometer signal, a motion sensor signal, and/or a neural imaging signal.

10. The method of claim 1, wherein applying the first electrical stimulation signal occurs while the patient is performing a behavioral therapy.

11. The method of claim 1, further comprising:
    interrupting application of the first electrical stimulation signal; and
    resuming application of the first electrical stimulation signal in the event that evidence of the collateral neural activity is absent.

12. The method of claim 1 wherein automatically determining whether collateral neural activity exists includes automatically determining whether collateral neural activity causally linked to the first electrical stimulation signal exists.

13. The method of claim 1 wherein:
    applying the first electrical stimulation signal includes applying the first electrical stimulation signal at a sub-threshold level from an electrode positioned within the patient's skull and external to a cortical surface of the patient's brain, as part of a treatment regimen that also includes directing the patient to engage in a behavorial therapy; and wherein
    responding to collateral neural activity includes discontinuing application of the first electrical stimulation signal and applying a second signal to inhibit the collateral neural activity.

14. The method of claim 13 wherein the behavioral therapy includes a cognitive task.

15. The method of claim 13 wherein the first electrical simulation signal is delivered from an electrode, and wherein the method further comprises receiving an indication of the collateral neural activity via the electrode.

16. The method of claim 13 wherein the electrode is positioned to be in contact with the patient's dura matter.

17. The method of claim 13 wherein the electrode is positioned to be in contact with the patient's pia matter.

* * * * *